United States Patent [19]

Yu et al.

[11] Patent Number: 5,246,857
[45] Date of Patent: Sep. 21, 1993

[54] CIRCULAR PLASMIDS DERIVED FROM THE GENUS RHODOCOCCUS

[75] Inventors: Fujio Yu, Yokohama; Yoshihiro Hashimoto, Tokyo, both of Japan

[73] Assignee: Nitto Chemical Industry Co., Ltd., Japan

[21] Appl. No.: 773,055

[22] Filed: Oct. 8, 1991

[30] Foreign Application Priority Data

Oct. 11, 1990 [JP] Japan ................................. 2-270377
Mar. 4, 1991 [JP] Japan ................................. 3-37546

[51] Int. Cl.$^5$ ....................... C12N 15/74; C12N 15/00
[52] U.S. Cl. ............................... 435/320.1; 435/172.3
[58] Field of Search ............... 435/172.3, 320.1, 252.3

[56] References Cited

U.S. PATENT DOCUMENTS 4,920,054 4/1990 Kozlowski ..................... 435/252.31
4,952,500 8/1990 Finnerty ............................. 435/69.1

FOREIGN PATENT DOCUMENTS 0186069 12/1985 European Pat. Off. .

OTHER PUBLICATIONS

Singer, M. E. et al., 1988, J. Bacteriol. 170:638–645.
Kusaka et al., 1988, Biol. Abstracts 85(1), abstract 3791.
Mil'ko et al., 1990, Biol. Abstracts 89(7), abstract 70218.
Dabbs et al., 1988, Biol. Abstracts 85(8), abstract 78582.
Desomer et al., J. Bacteriol., 170(5):2401–2405 (1988).
Desomer et al., Appl. & Environ. Microbiol., 56:2818–2825 (1990).
Dobbs et al, Mol. Gen. Genet., 211:148–154 (1988).
Vogt Singer et al., J. Bacteriol., 170(2):638–645 (1988).
Goodfellow et al., J. Gen. Microbiol., 100:99–122 (1977).
ATCC Catalogue of Bacteria, Phages and r DNA vectors, 16th edition, pp. 150.

*Primary Examiner*—Richard A. Schwartz
*Assistant Examiner*—Nancy T. Vogel
*Attorney, Agent, or Firm*—Pennie & Edmonds

[57] ABSTRACT

The present invention provides an isolated circular plasmid of about 2.6 kb derived from a bacterium belonging to the genus Rhodococcus whose restriction sites compises two SacI sites, one BamII site, one PvuI site, one ScaI site, one SphI site and one XhoI site. In addition, the present invention provides an isolated circular plasmid of about 7.6 kb derived from a bacterium belonging to the genus Rhodococcus whose restriction sites compises one SphI site, two KpnI sites, one BglII site, and three SacI sites. The vectors of the invention can be suitable for Rhodococcus hosts and usefull in industry.

6 Claims, 2 Drawing Sheets

CIRCULAR PLASMIDS DERIVED FROM THE GENUS RHODOCOCCUS

FIELD OF THE INVENTION

The present invention relates to novel plasmids, specifically plasmids derived from bacteria belonging to the genus Rhodococcus.

BACKGROUND OF THE INVENTION

Bacteria belonging to the genus Rhodococcus have been known to hydrate nitrils to amides or acids. Also, certain strains belonging to *Rhodococcus rhodochrous* have been known to contain a nitril hydration activity.

However, vectors suitable for Rhodococcus hosts have not been developed yet and, in reality, few vectors are available from very few sources such as Rhodococcus sp. H13-A (J. Bacteriol., 1988, 170:638-645) to date. To utilize the useful properties of the bacteria, vectors suitable for Rhodococcus hosts and subsequent industrial use have been long awaited.

SUMMARY OF THE INVENTION

The present inventors have investigated bacteria belonging to Rhodococcus that contain vectors suitable for hosts and industrial use and successfully found circular plasmids suitable as vectors. The present invention provides an isolated circular plasmid of abut 2.6 kb derived from a bacterium belonging to the genus Rhodococcus whose restriction sites compises tow SacI sites, one BamHI site, on PvuI site, one ScaI site, one SphI site and one XhoI site. In addition, the present invention provides an isolated circular plasmid of about 7.0 kb derived from a bacterium belonging to Rhodococcus sp. whose restriction sites compises one SphI site, two KpnI sites, one BglII site, and three SacI sites.

DETAILED DESCRIPTION OF THE INVENTION

Figure 1:
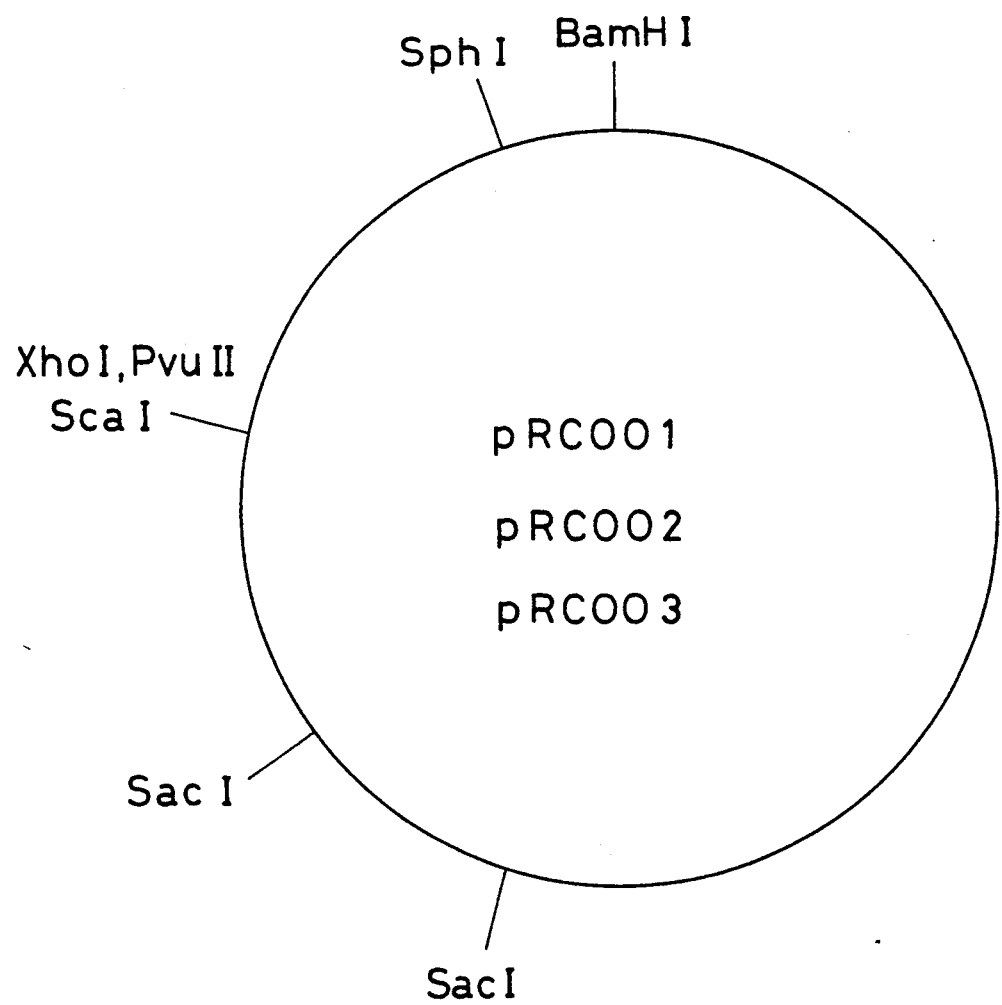
FIG. 1 shows a restriction map of plasmid pRC001, pRC002, and pRC003.
Figure 2:
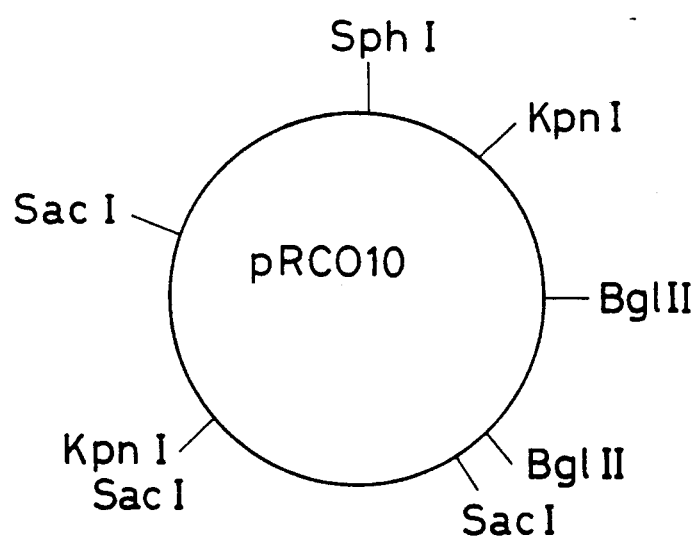
FIG. 2 shows a restriction map of plasmid pRC010.

Novel plasmids, pRC001, pRC002, and pRC003, are derived from *Rhodococcus rhodochrous* ATCC 4276, ATCC 14349 or ATCC 14348, respectively. A culture of each *Rhodococcus rhodochrous* (ATCC 4001) (Mar. 1, 1927), *R. rhodochrous* (ATCC 4276) (Apr. 4, 1928), *R. rhodochrous (ATCC 14348)* (Jan. 1, 1943), and *R. rhodochrous (ATCC 14349)* (Jan. 1, 1943), has been deposited with and is publicly available from the American Type Tissue Culture Collection, 12301 Parklawn Drive, Rockville Md. The sizes of the plasmids are all about 2.6 kb. Table 1 shows numbers of restriction sits and sizes of restriction fragments.

TABLE 1

| Restriction enzyme | Number of restriction Sites | Size (kb) |
| --- | --- | --- |
| SacI | 2 | 2.3, 0.3 |
| BamHI | 1 | 2.6 |
| PvuII | 1 | 2.6 |
| ScaI | 1 | 2.6 |
| SphI | 1 | 2.6 |
| XhoI | 1 | 2.6 |

A novel circular plasmid pRC010 is derived from *Rhodococcus rhodochrous ATCC 4001*. The size of the plasmid is about 7.0 kb. Table 2 shows numbers of restriction sites and sizes of restriction fragments.

TABLE 2

| Restriction enzyme | Number of restriction Sites | Size (kb) |
| --- | --- | --- |
| SphI | 1 | 7.0 |
| KpnI | 2 | 4.0, 3.0 |
| BglII | 2 | 6.5, 0.5 |
| SacI | 3 | 4.2, 2.0, 0.8 |

Examples

The following examples will further describe the invention.

EXAMPLE 1

(1) Isolation and Purification of Plasmid

Each of *Rhodococcus rhodochrous* ATCC 4276, ATCC 14349 or ATCC 14348 was grown in 400 ml of a MY medium (0.5% polypepton, 0.3% bactoyeast extract, 0.3% malt extract, 1% glucose). When $OD_{660}$ reached 0.15-0.2, 0.5 U/ml of penicillin G was added to the culture. The culture was further incubated until $OD_{600}$ of 1.0. After incubation, bacterial cells were harvested by centrifugation, washed with 40 ml of a TES buffer (10 mM Tris-HCl/pH 8, 10 mM NaCl, 1 mM EDTA), and then suspended in 11 ml of a solution containing 50 mM Tris-HCl/pH 8, 12.5% sucrose, 100 mM NaCl, 1 mg/ml of lysozyme. The suspension was incubated with shaking at 37° C. for 3 hours. 0.6 ml of 0.5M EDTA, 2.4 ml of 5M NaCl, and 4.4 ml of 4% SDS/0.7M NaCl were added in the listed order to the bacterial cell lysate. The mixture was gently swirled and placed on ice for 18 hours. After incubation, the mixture was centrifuged at 4° C., at 65,000×g for an hour. After centrifugation, the supernatant was saved and then 4.6 ml of 50% polyethyleneglycol 6,000 was added to the supernatant. The mixture was placed on ice for 3 hours. After incubation, the mixture was centrifuged at 1,000×g for 5 minutes. The supernatant was discarded and the pellet was dissolved in 5 ml of a TES buffer and then 2 ml of a TES buffer containing 7.5 g of cesium chloride and 1.5 mg/ml of ethidium bromide was added to the pellet solution. The mixture was ultracentrifuged at 130,000×g for 42 hours. After ultracentrifugation, the fraction containing plasmids was removed under the UV light. The plasmid fraction was extracted with n-butanol to remove ethidium bromide. After extraction, the plasmid fraction was dialyzed against TE (10 mM Tris-HCl/pH 8, 1 mM EDTA) and then precipitated with ethanol. The plasmid thus obtained was electrophoresed on a 0.7% agarose gel. The gel was stained with ehidium bromide and examined under the UV light. The band containing plasmids was found on the gel.

(2) Determination of Molecular Weight of Plasmid

Plasmids were electrophoresed along with pUC18 (2.69 kb), pUC 118 (3.16 kb), and pBR322 (4.36 kg) as markers on a 0.7% agarose gel. The sizes of plasmids were all about 2.6 kb. Plasmids were designated as pRC001 (ATCC 427), pRC002 (ATCC 14349) and pRC 003 (ATCC 14384). The parenthesis indicates the ATCC number of the *Rhodococcus rhodochrous* source.

(3) Numbers and Sizes of Restriction Sites of Plasmids

Plasmids, pRC001, pRC002 and pRC 003, were digested with various restriction enzymes and restriction fragments were electrophoresed along with markers such as HindIII- and PstI-digested lambda phase DNA on 0.7% agarose gel and 5% acrylamide gel. The results are shown in Table 3.

TABLE 3

| Restriction enzyme | Number of restriction Sites | Size (kb) |
|---|---|---|
| SacI | 2 | 2.3, 0.3 |
| BamHI | 1 | 2.6 |
| PvuII | 1 | 2.6 |
| ScaI | 1 | 2.6 |
| SphI | 1 | 2.6 |
| XhoI | 1 | 2.6 |
| EcoRI | 0 | — |
| HindIII | 0 | — |
| KpnI | 0 | — |

EXAMPLE 2

(1) Isolation and Purification of Plasmid

*Rhodococcus rhodochrous* ATCC 4001 was grown in 400 ml of a MY medium (0.5% polypepton, 0.3% bactoyeast extract, 0.3% malt extract, 1% glucose). When $OD_{660}$ reached 0.15-0.2, 0.5 U/ml of penicillin G was added to the culture. The culture was further incubated unitll $OD_{660}$ of 1.0. After incubation, bacterial cells were harvested by centrifugation, washed with 40 ml of a TES buffer (10 mM Tris-HCl/pH 8, 10 mM NaCl, 1 mM EDTA), and then suspended in 11 ml of a solution containing 50 mM Tris-HCl/pH 8, 12.5% sucrose, 100 mM NaCl, 1 mg/ml of lysozyme. The suspension was incubated with shaking at 37° C. for 3 hours. 0.6 ml of 0.5M EDTA, 2.4 ml of 5M NaCl, and 4.44 ml of 4% SDS/0.7M lysate. The mixture was gently swirled and placed on ice for 18 hours. After incubation, the mixture was centrifuged at 4° C., at 65,000×g for an hour. After centrifugation, the supernatant was saved and then 4.6 ml of 50% polyethyleneglycol 6,000 was added to the supernatant. The mixture was placed on ice for 3 hours. After incubation, the mixture was centrifuged at 1,000×g for 5 minutes. The supernatant was discarded and the pellet was dissolved in 5 ml of a TES buffer and then 2 ml of a TES buffer containing 7.5 g of cesium chloride and 1.5 mg/ml of ethidium bromide was added to the pellet solution. The mixture was ultracentrifuged at 130,000×g for 42 hours. After ultracentrifugation, the fraction containing plasmids was removed under the UV light. The plasmid fraction was extracted with n-butanol to remove ethidium bromide. After extraction, the plasmid fraction was dialyzed against TE (10 mM Tris-HCl/pH 8, 1 mM EDTA) and the precipitated with ethanol. The plasmid thus obtained was electrophoresed on a 0.7% agarose gel. The gel was stained with ehidium bromide and examined under the UV light. The band containing plasmids was found on the gel.

(2) Determination of Molecular Weight of Plasmid

Plasmids were electrophoresed along with pUC18 (2.69 kb), pUC 118 (3.16 kb), and pBR322 (4.36 kb) as markers on a 0.7% kb. The plasmid was designated as pRC010 (ATCC 4001). The parenthesis indicates the ATCC number of the *Rhodococcus rhodochrous* source.

(3) Numbers and Sizes of Restriction Sites of Plasmids

Plasmid pRC010 was digested with various restriction enzymes and restriction fragments were electrophoresed along with markers such as HindIII- and PstI-digested lambda phase DNA on 0.7% agarose gel and 5% acrylamide gel. The results are shown in Table 4.

TABLE 4

| Restriction enzyme | Number of restriction Sites | Size (kb) |
|---|---|---|
| SphI | 1 | 7.0 |
| KpnI | 2 | 4.0, 3.0 |
| BglII | 2 | 6.5, 0.5 |
| SacI | 3 | 4.2, 2.0, 0.8 |
| BamHI | 0 | — |
| BclI | 0 | — |
| EcoRI | 0 | — |
| HindIII | 0 | — |
| ClaI | 0 | — |
| PvuII | 0 | — |
| PstI | 0 | — |
| ScaI | 0 | — |
| SmaI | 0 | — |

What is claimed is:

1. An isolated circular plasmid of about 2.6 kb obtained from *Rhodococcus rhodochrous* ATCC 4276, ATCC 14349 or ATCC 14348, the restriction sites of said circular plasmid which comprises two SacI sites, one BamHI site, one PvuI site, one ScaI site, one SphI site and one XhoI site.

2. The isolated circular plasmid of claim 1 which is plasmid pRC001.

3. The isolated circular plasmid of claim 1 which is plasmid pRC002.

4. The isolated circular plasmid of claim 1 which is plasmid pRC003.

5. An isolated circular plasmid of about 7.0 kb obtained from *Rhodococcus rhodochrous* ATCC 4001, the restriction sites of said circular plasmid which comprise one SphI site, two KpnI sites, two BglII sites and three SacI sites.

6. The isolated circular plasmid of claim 5 which is plasmid pRC010.

* * * * *